US00PP27755P3

(12) United States Plant Patent
Geers

(10) Patent No.: US PP27,755 P3
(45) Date of Patent: Mar. 7, 2017

(54) ***ILEX×MESERVEAE* PLANT NAMED 'GEERS'**

(50) Latin Name: *Ilex×meserveae*
Varietal Denomination: GEERS

(71) Applicant: Peter Geers, Boskoop (NL)

(72) Inventor: Peter Geers, Boskoop (NL)

( * ) Notice: Subject to any disclaimer, the term of this patent is extended or adjusted under 35 U.S.C. 154(b) by 0 days.

(21) Appl. No.: 14/545,936

(22) Filed: Jul. 8, 2015

(65) Prior Publication Data

US 2017/0013753 P1 Jan. 12, 2017

(51) Int. Cl.
*A01H 5/00* (2006.01)

(52) U.S. Cl.
USPC ..... Plt./247

(58) Field of Classification Search
USPC ..... Plt./247
See application file for complete search history.

*Primary Examiner* — Susan McCormick Ewoldt
(74) *Attorney, Agent, or Firm* — Cassandra Bright

(57) ABSTRACT

A new and distinct *Ilex×meserveae* cultivar named 'GEERS' is disclosed, characterized by greyed-green leaves margined cream-white with dotted transition. Plants are male and do not produce fruit. Floriferous plants with moderately vigorous growth. Leaves appear sharp but are not sharp to the touch. The new variety is an *Ilex×meserveae*, normally produced as an outdoor garden plant.

2 Drawing Sheets

Figure 1:
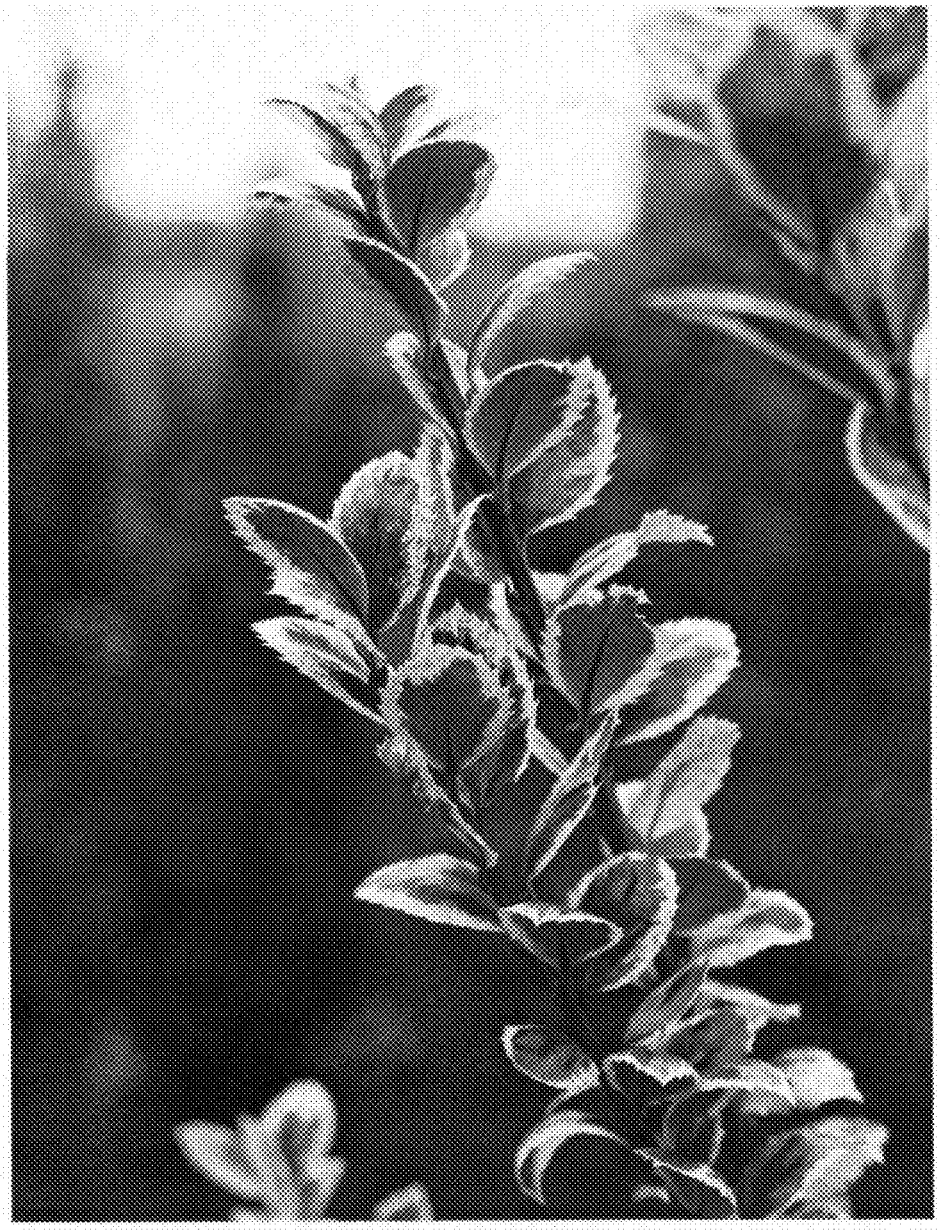

Latin name of the genus and species: *Ilex×meserveae*.
Variety denomination: 'GEERS'.

BACKGROUND OF THE INVENTION

The new cultivar is the product of chance discovery. The new variety originated as a naturally occurring branch mutation of the patented commercial variety *Ilex×meserveae* 'Blue Prince' U.S. Plant Pat. No. 3,517 (patent terminated).

The new variety was discovered in Summer of 1995 by the inventor Peter Geers a citizen of Netherlands in a nursery in Boskoop, Netherlands.

Asexual reproduction of the new cultivar was performed by softwood cuttings. This was first performed at a nursery in Boskoop, Netherlands in August of 1995 and has shown that the unique features of this cultivar are stable and reproduced true to type in 10 successive generations.

SUMMARY OF THE INVENTION

The cultivar 'GEERS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GEERS' These characteristics in combination distinguish 'GEERS' as a new and distinct *Ilex×meserveae* cultivar:

1. Greyed-green leaves margined cream-white.
2. Transition from greyed-green to cream-white not clear and precise, but with a somewhat dotted variegation in the greyed-green part.
3. Moderately vigorous growth.
4. Leaves look sharp to the touch but are not.
5. Very floriferous.
6. No fruit (male variety).

Plants of the new cultivar 'GEERS' are similar to plants of the seed parent, *Ilex×meserveae* 'Blue Prince' U.S. Plant Pat. No. 3,517 (patent terminated), in most horticultural characteristics, however, plants of the new cultivar 'GEERS' differ in the following;

1. The new variety has greyed-green leaves margined with cream-white whereas the parent has dark green leaves that are not variegated.

COMMERCIAL COMPARISON

Plants of the new cultivar 'GEERS' are comparable to the patented commercial variety *Ilex* 'Casanova' U.S. Plant Pat. No. 19,573. The two *Ilex* varieties are similar in most horticultural characteristics; however, the new variety 'GEERS' differs in the following:

1. Leaf color of the new variety is greyed-green margined cream white whereas the comparator has dark green leaves margined in cream-white.
2. Transition from greyed-green to cream-white is not precise in the new variety, whereas the comparator has a clear and precise transition from dark green to cream-white.
3. Transition from grey-green to cream with a somewhat dotted variegation in the greyed-green parts. The comparator transition is without dotted variegation.

Plants of the new cultivar 'GEERS' can also be comparable to the unpatented commercial variety *Ilex* 'Golden Prince'. The two *Ilex* varieties are similar in most horticultural characteristics; however, the new variety 'GEERS' differs in the following:

1. Leaf color of the new variety is greyed-green margined cream white whereas the comparator has dark olive green leaves broadly margined in golden yellow.
2. Transition from greyed-green to cream-white is not precise in the new variety, whereas the comparator has a clear and precise transition from dark olive green to golden yellow.
3. Transition from grey-green to cream with a somewhat dotted variegation in the greyed-green parts. The comparator transition is without dotted variegation.

Plants of the new cultivar 'GEERS' can also be compared to the commercial variety *Ilex* 'Blue Baron', U.S. Plant Pat. No. 16,151. The two *Ilex* varieties are similar in most horticultural characteristics; however, the new variety 'GEERS' differs in the following:

1. Leaf color of the new variety is greyed-green margined cream white whereas the comparator has solid green foliage.
2. Plants of the new variety, while dense are not as compact/short as plants of 'Blue Baron'.

BRIEF DESCRIPTION OF THE PHOTOGRAPHS

The accompanying photograph in FIG. 1 illustrates in full color close up of the foliage.

Figure 2:
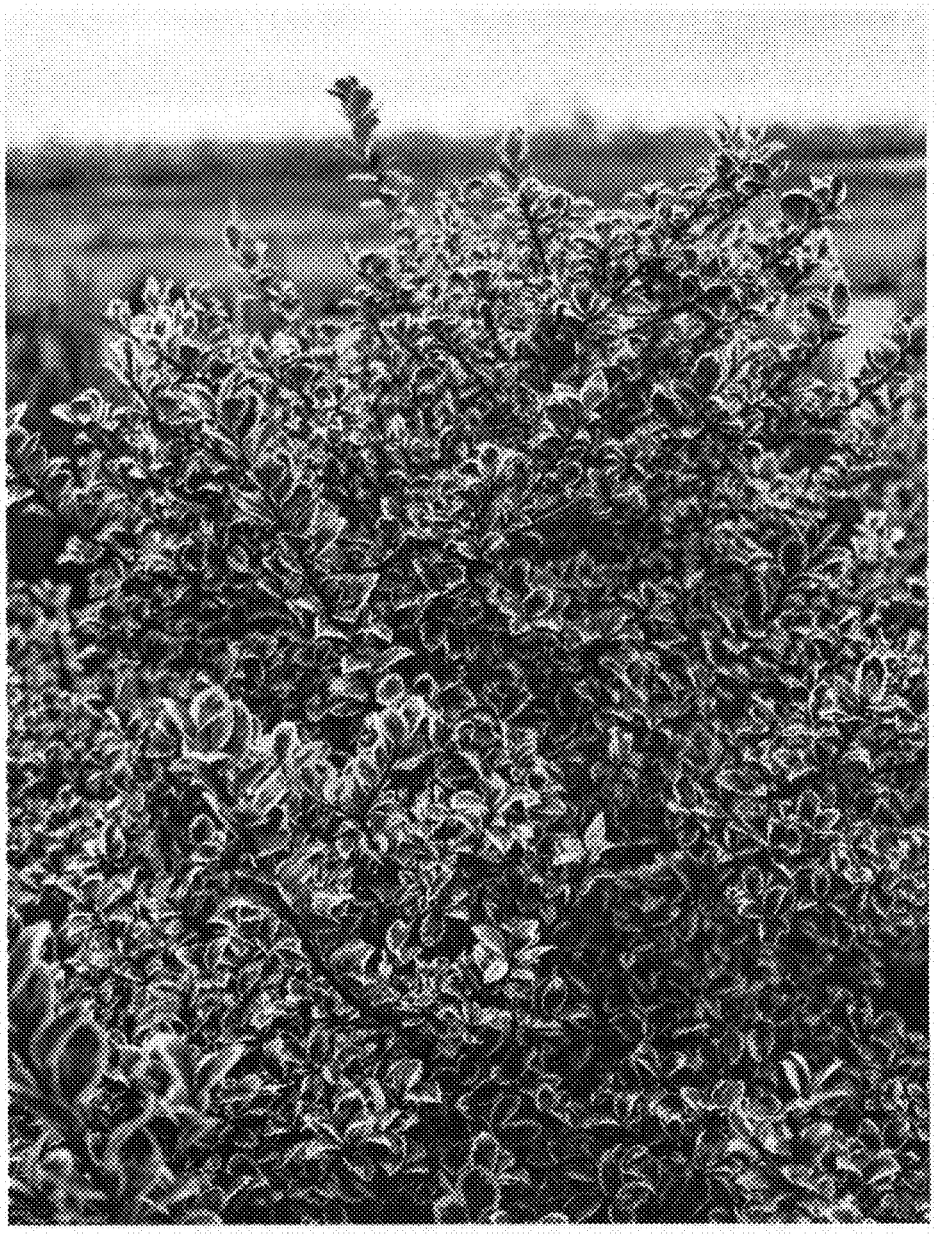

FIG. 2 illustrates a plant of the new variety. The plant photographed is approximately 1 year old from a 2¼ inch liner grown outdoors in Grand Haven, Mich.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1995 except where general terms of ordinary dictionary significance are used. The following observations and measurements describe 'GEERS' plants grown in March in a poly greenhouse, in Grand Haven, Mich., USA. The growing temperature ranged from 17° C. to 27° C. during the day and from 5° C. to 10° C. during the night. General light conditions are bright, normal sunlight. Measurements and numerical values represent averages of typical plant types.

Botanical classification: *Ilex×meserveae* 'GEERS'.

PROPAGATION

Type of propagation typically used: Softwood cutting.

Time to initiate roots: 100 days during Winter.

Time to produce a rooted young plant during the winter: 1 year.

Root description: Moderately dense, moderately free-branching, medium thickness, non-fibrous, non-fleshy. Color is Grey-white, not accurately measured with the R.H.S. chart.

PLANT

Age of plant described: Approximately 1-2 years from rooted cutting.

Plant type: Perennial shrub.

Container size of the plant described: #1.

Appropriate containers: 1, 2, 3, 5 gallon commercial containers.

Growth habit: Upright and slightly outward.

Overall plant shape: Upright plants, do not mature to a round form.

Height: 26 cm at 1 year from a rooted liner.

Plant spread: 24 cm at 1 year from a rooted liner.

Growth rate: Moderate.

Plant vigor: Good.

Characteristics of primary lateral branches:

*Quantity.*—10 in a 1 gallon container, in early growth stage.

*Branching habit.*—Good spatial orientation, basal branching pinching required.

*Branch appearance.*—1 year old stems often 5 sided, pentagon shaped. Stems 2 years and older become rounded.

*Length.*—19 cm — in a 1 gallon pot at 1 year from a rooted liner.

*Diameter.*—5 mm — in a 1 gallon pot at 1 year from a rooted liner.

*Color.*—New growth: Base color RHS Red-purple 59A with striations on flat edges in Greyed-purple 187A. Mature growth: Faint base of Greyed-purple 187A with several striations in a faint Greyed-purple 187D, distributed on all sides.

*Pubescence.*—None.

*Stem aspect/angle.*—0° to 35° angle of attachment.

*Strength.*—Rigid.

*Other branch characteristics.*—Farinose near base of older growth.

Internode length: Old wood 2.5 cm, new wood 1 to 2 cm.

FOLIAGE

Leaf:

*Arrangement.*—Alternate, single.

*Average length.*—Young: 2.5 cm; Mature: 6 cm.

*Average width.*—Young: 1.5 cm; Mature; 3.5 cm.

*Shape.*—Ovate.

*Apex.*—Acute.

*Base.*—Cuneate to obtuse.

*Margin.*—Serrate.

*Texture of top surface.*—Mature: Smooth, waxy, coriaceous. Young: Smooth, slightly coriaceous.

*Texture of bottom surface.*—Mature: Smooth, slightly waxy, distinct central vein. Young: Smooth, slightly waxy.

*Pubescence.*—None.

*Color.*—Young foliage upper side: Base color RHS Greyed-green 189A slight bleeding away from central vein in Green 139A. Water-color fade near outer edge of margin in Greyed-green 194C. Inner side of margin Yellow 11C fading into Yellow 11B towards outer edge of margin. Minimal spotting on margin in Greyed-green 189A. Young foliage under side: Base color RHS Greyed-green 194B slight bleeding away from central vein in Greyed-green 191A. Base appears in water-color fade. Margin color Yellow 11A Minimal spotting on margin in Greyed-green 191A. Mature foliage upper side: Base color RHS Greyed-green 189A bleeding into Green 139A, appears in a water-color fade, both colors bleed into the margin loosely-no rigid border. Inner edge of margin Yellow 11C, faintly fading to outer edge of margin in Yellow 11B, base of leaf margin extends outward from petiole in Greyed-purple 187C. Light spotting on margin in Green 137C, spotting slightly clustered, and distributed throughout entire margin. Mature foliage under side: Base color RHS Greyed-green 191C, bleeding away from central vein into Green 138B-base appears in a water-color fade. Inner margin yellow 11C, blending into a soft fade of Yellow 11B. Spotting on margin in Green 137D, spotting slightly clustered and distributed throughout entire margin.

*Venation*.—Type: Opposite pinnate. Venation color upper side: Young: RHS Green 137D. Mature: RHS Yellow-green 144A. Venation color under side: Young: RHS Green 138B, central vein Green 137B. Mature: RHS Green 137C, central vein Greyed-purple 187B blending into Greyed-purple 187C to Green 137B.

*Petiole*.—Length: Young: 4.5 mm. Mature 6 mm. Diameter: Young: 1 mm. Mature 2 mm. Color: Upper side: Young: RHS Greyed-purple 186B. Mature: RHS Greyed-purple 186B. Lower side: Young: RHS Greyed-purple 186B. Mature: Greyed-purple 187A blending to 187B.

*Texture*.—Upper side: Smooth. Lower side: Smooth.

*Spines*.—Spines protruding from serrate edge of leaf margin, 025 mm in length.

*Other traits*.—Small clustered budding at the base of each node in RHS Greyed-purple 187C.

FLOWER

Flower arrangement: Rotate.
Flower shape: Rotate.
Natural flowering season: Early Spring.
Persistent or self-cleaning: Self-cleaning.
Quantity of flowers per cluster: 2-5.
Bud:
*Shape*.—Spherical-oblong.
*Length*.—3 mm.
*Diameter*.—2 mm.
*Color*.—Near RHS Red 51B.
Flower size:
*Diameter*.—4 mm.
*Length*.—9 mm.
Petals:
*Appearance*.—Soft and smooth.
*Arrangement*.—Whorled.
*Petal length*.—4 mm.
*Petal width*.—3 mm.
*Quantity*.—5-6.
*Texture*.—Smooth.
*Apex*.—Obtuse.
*Shape*.—Oblong.
*Base*.—Obtuse.
*Margin*.—Entire.
*Aspect*.—Outward.
Petal color:
*When opening*.—Upper surface: RHS White 155D. Lower surface: RHS White 155D.
*Fully opened*.—Upper surface: RHS White 155D. Lower surface: RHS White 155D.
*Fading to color*.—Upper and lower: RHS White 155D.
Sepals:
*Quantity per flower*.—4.
*Arrangement*.—Whorl.
*Shape*.—Obovate.
*Length*.—1 mm.
*Width*.—1 mm.
*Apex*.—Entire.
*Base*.—Acute.
*Margin*.—Truncate.
*Color*.—Upper Surface: RHS Yellow-green 145B. Lower Surface: RHS Yellow-green 145B.
Pedicel:
*Length*.—4 mm.
*Diameter*.—1 mm.
*Color*.—RHS Yellow-green 145B.
*Angle*.—Facing out and upward.
*Texture*.—Average.

REPRODUCTIVE ORGANS

Stamens:
*Number*.—4.
Anthers:
*Shape*.—Elliptic.
*Length*.—Less than 1 mm.
*Color*.—RHS White 155C.
*Pollen*.—Color: Scant, not accurately measured with R.H.S. chart. Quantity: Scant.
Pistil:
*Number*.—1.
*Length*.—3 mm.
*Style*.—Length: 3 mm. Color: RHS Yellow-green 144B.
*Stigma*.—Shape: Circular. Color: RHS Yellow-green 151A. Ovary Color: RHS Yellow-green 151C.

OTHER CHARACTERISTICS

Seeds and fruits: No fruits, male variety.
Disease/pest resistance: Neither resistance nor susceptibility to the normal diseases and pests of *Ilex* has been observed.
Lowest temperature tolerance: At least to USDA zone 6.
Highest temperature tolerance: At least to USDA zone 9.
Garden performance: Excellent garden performance; very tolerant to rain and wind.

What is claimed is:

1. A new and distinct cultivar of *Ilex×meserveae* plant named 'GEERS' as herein illustrated and described.

* * * * *